United States Patent [19]
Arod et al.

[11] 4,105,508
[45] Aug. 8, 1978

[54] METHOD AND DEVICE FOR ANALYSIS OF A MIXTURE OF HYDROCHLORIC ACID AND ORGANOCHLORINE COMPOUNDS CONTAINED IN GASES DERIVED IN PARTICULAR FROM THE INCINERATION OF ORGANOCHLORINE COMPOUNDS

[75] Inventors: Jean Arod, Pierrevert; Michèle Gauthier, Aix en Provence; Roger Platzer, Chatillon, all of France

[73] Assignee: Commissariat a l'Energie Atomique, Paris, France

[21] Appl. No.: 780,717

[22] Filed: Mar. 24, 1977

[30] Foreign Application Priority Data
Apr. 2, 1976 [FR] France .................. 76 09625

[51] Int. Cl.² ............. G01N 27/42; G01N 31/12
[52] U.S. Cl. ................. 204/1 T; 23/230 PC; 23/232 E; 23/253 PC; 23/254 E; 204/195 R
[58] Field of Search ........ 23/230 PC, 253 PC, 232 E, 23/254 E, 255 E; 204/1 T, 1 B, 195 R

[56] References Cited
U.S. PATENT DOCUMENTS

| | | | |
|---|---|---|---|
| 2,384,368 | 9/1945 | Crouch et al. | 23/232 E |
| 2,593,878 | 4/1952 | Haines et al. | 23/232 E |
| 3,001,917 | 9/1961 | Scheirer | 23/232 E X |
| 3,111,392 | 11/1963 | Stout, Jr. | 23/255 E |
| 3,355,252 | 11/1967 | De Bliek | 23/230 PC X |
| 3,546,079 | 12/1970 | Waclawik et al. | 23/232 E X |
| 3,997,416 | 12/1976 | Confer | 23/232 E |

*Primary Examiner*—Joseph Scovronek
*Attorney, Agent, or Firm*—Sidney W. Millard

[57] ABSTRACT

The gases are passed through a cell containing a first solution for dissolving the hydrochloric acid, subjected to coulometric measurement of the chloride ion content Q, passed through a vessel for absorbing the hydrochloric acid and chlorine, the organochlorine compounds contained in the remaining gases being then burnt in a combustion chamber. The combustion gases are passed through a second solution for dissolving the hydrochloric acid liberated by the organochlorine compounds, subjected to a second coulometric measurement of the chloride ion content q, the ratio q/Q being determined by a computer.

33 Claims, 2 Drawing Figures

METHOD AND DEVICE FOR ANALYSIS OF A MIXTURE OF HYDROCHLORIC ACID AND ORGANOCHLORINE COMPOUNDS CONTAINED IN GASES DERIVED IN PARTICULAR FROM THE INCINERATION OF ORGANOCHLORINE COMPOUNDS

This invention relates to a method and a device for analyzing a mixture of hydrochloric acid and organochlorine compounds contained in gases derived for example from the incineration of organochlorine compounds.

The method and the device in accordance with this invention are primarily intended to control the destruction of organochlorine compounds by incineration and are particularly well suited to the construction of a system for automatic control of a destruction process of this type by means of successive analyses of fractions of the incineration gases.

It is recalled that the quality of a destruction of organochlorine compounds by incineration can be evaluated by determining in the incineration gases the quantity of organochlorine compounds which have not been destroyed and the quantity of hydrochloric acid which has been liberated at the time of incineration; the quality of the destruction can be designated by the ratio of the quantities mentioned above.

The method in accordance with the invention for the analysis of a mixture of hydrochloric acid and of organochlorine compounds contained in gases derived in particular from the incineration of organochlorine compounds essentially consists:

in passing said gases through a solution or so-called first solution which is capable of dissolving the hydrochloric acid;

in measuring the quantity of chloride ions Q contained in said first solution by coulometry;

in absorbing the hydrochloric acid and the chlorine which are present in the remaining gases after these latter have passed through said first solution;

in initiating combustion of the remaining gases after absorption of the hydrochloric acid and the chlorine which are present in these latter in order to burn the entire quantity of organochlorine compounds contained in said remaining gases;

in passing the gases produced by combustion of the remaining gases through a solution or so-called second solution which is capable of dissolving the hydrochloric acid liberated by the organochlorine compounds at the time of said combustion of remaining gases;

in measuring the quantity of chloride ions q contained in said second solution by coulometry;

in calculating the ratio $q/Q$.

The main advantage of the method in accordance with the invention as characterized in the foregoing lies in the fact that the measurements of $q$ and $Q$ can be taken in the same stream of gas.

It can be noted that, in accordance with this method, the measurement of said quantities $q$ and $Q$ is advantageously carried out by specific coulometry of chloride ions, that is to say by measuring a quantity of electricity at the time of electrolysis at controlled intensity. By means of this coulometric measurement, it will be possible in particular to choose at will the length of time during which the gases are passed through said first and second solutions.

In accordance with an advantageous feature of the invention, the method is further distinguished by the fact that, after the gases have been passed through the solutions, any organochlorine compounds which may have been retained in said first solution are entrained by passing a carrier gas through this latter.

In accordance with the invention, said first solution which is capable of dissolving hydrochloric acid is preferably an alkaline solution of sodium bicarbonate and sodium sulphate having a pH value which is preferably of the order of 8.6, the sodium sulphate being intended to reduce the solubility of the organochlorine compounds in said solution.

The method of analysis in accordance with the invention as characterized in the foregoing can advantageously be employed for sequential analysis of a mixture of hydrochloric acid and organochlorine compounds contained in gases.

This method of sequential analysis is distinguished by the fact that predetermined fractions of said gases corresponding to a given variation of the pH value of said first solution are analyzed successively by passing said fractions through said first solution.

The invention is also concerned with a device for analyzing a mixture of hydrochloric acid and organochlorine compounds contained in gases, said device being characterized in that it comprises:

a cell containing a solution or so-called first solution which is capable of dissolving the hydrochloric acid;

means for introducing said first solution into said cell;

means for passing said gases through said first solution;

at the outlet of said cell, a first coulometric cell for measuring the quantity of chloride ions Q contained in said first solution;

at the outlet of said cell, absorption means for absorbing the hydrochloric acid and the chlorine which are present in the remaining gases after these latter have passed through said first solution;

at the outlet of said absorption means, a combustion chamber for the remaining gases in order to ensure that the organochlorine compounds contained in said remaining gases are completely burnt;

at the outlet of said chamber, means for passing the combustion gases produced by said remaining gases through a so-called second solution which is capable of dissolving the hydrochloric acid liberated by the organochlorine compounds at the time of said combustion of remaining gases, and a second coulometric cell for measuring the quantity of chloride ions q contained in said second solution, the solution of said second coulometric cell being intended to constitute said second solution;

thermostatically controlled means associated with said cell and with said means for measuring $a$ and Q;

means for calculating $q/Q$.

In one advantageous embodiment of the invention, the device aforesaid is essentially provided in addition with means for causing air to pass through said cell after the gases have been passed through this latter.

Furthermore, in accordance with the invention, said cell of the device is so designed as to ensure good homogenization of said first solution which is capable of dissolving the hydrochloric acid with agitation. To this end, the cell is provided internally with a toric body of suitable shape.

In a preferential embodiment of the device in accordance with the invention, the device is essentially provided in addition with means for passing through said first solution a predetermined fraction of said gases corresponding to a given variation of the pH value of said first solution by passing said fraction through said first solution.

In accordance with another preferential embodiment, the device is characterized in that it comprises in addition:

means for initiating the analysis of a given fraction of said gases, means for storing the results of said analysis in memory, means for initiating a further analysis.

The device in accordance with the embodiment aforesaid makes it possible to carry out in a satisfactory manner the automatic sequential analysis of a mixture of hydrochloric acid and organochlorine compounds and consequently to control the incineration of organochlorine compounds.

Further distinctive features and advantages of the present invention will be more clearly brought out by the following description of one example of practical application which is given by way of explanatory illustration but not in any limiting sense and relates to the method and device in accordance with the invention for the analysis of a mixture of hydrogen chloride gases and organochlorine compounds contained in gases produced by incineration of organochlorine waste products withdrawn from the incinerator for example by means of a sampling tube of the type described in French patent Application No. EN 76 09624 filed in the name of the present Applicant on Apr. 2nd, 1976.

It can also be noted that the method and device in accordance with the invention can be utilized for the purpose of anaylzing a mixture of hydrochloric acid and organohalogen compounds.

The following description will be given with reference to the accompanying drawings, wherein.

Figure 1:
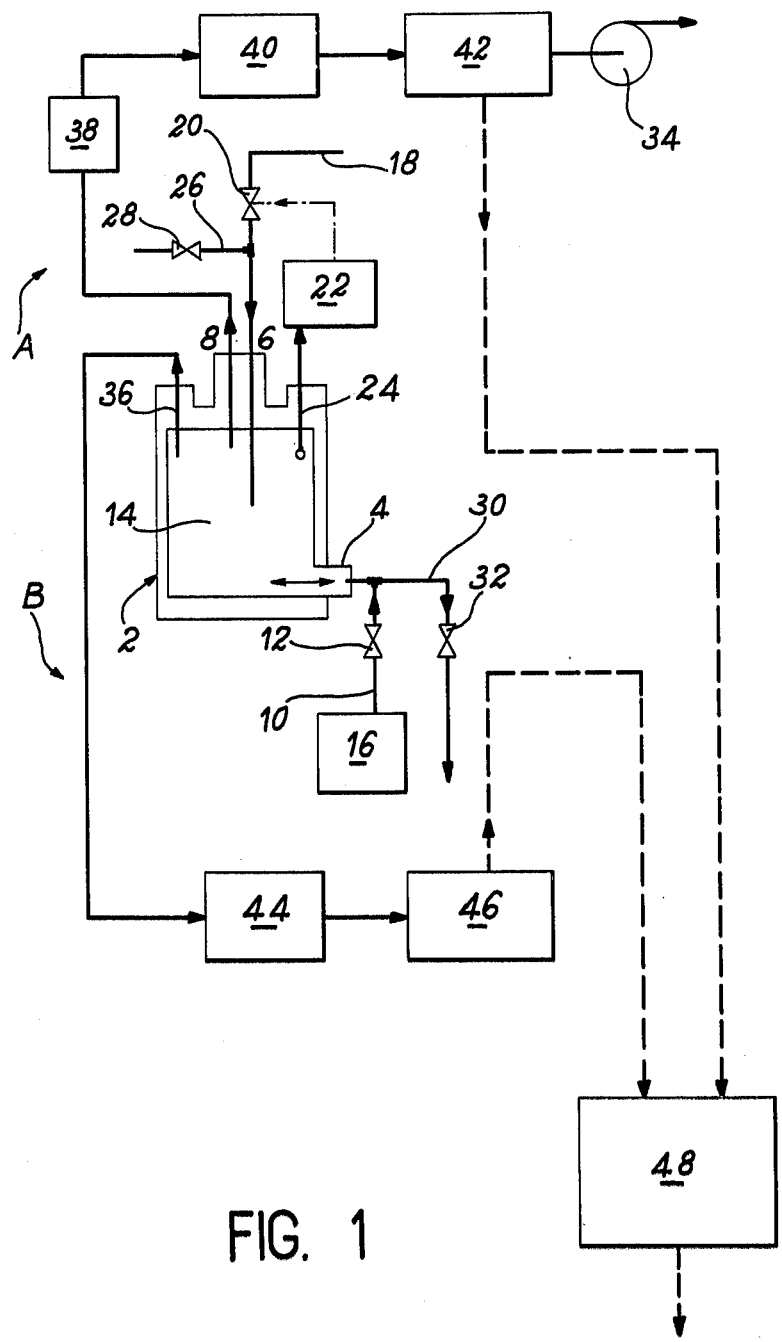
FIG. 1 is a general diagram of the device for analyzing a mixture of hydrochloric acid and organochlorine compounds contained in gases.

In FIG. 1, the reference numeral 2 designates a cell for continuously agitating a solution 14 which is introduced into said cell at 4 and intended to effect bubbling of gas containing a mixture of hydrochloric acid and organochlorine compounds, said gases being admitted into said cell 2 at 6 and discharged from this latter at 8. More precisely, the abovementioned solution 14 which is intended to dissolve the hydrochloric acid of said mixture at the time of bubbling of the gases is constituted by an alkaline solution of sodium bicarbonate and sodium sulphate. Said cell 2 is connected on the one hand by means of the pipe 10 fitted with a valve 12, a drawing-off pump and means for quantity determination (not shown) to a storage reservoir 16 for said solution 14 and on the other hand by means of the pipe 18 fitted with a valve 20 to a unit 18A for drawing-off the gases produced by incineration of organochlorine compounds.

Figure 2:
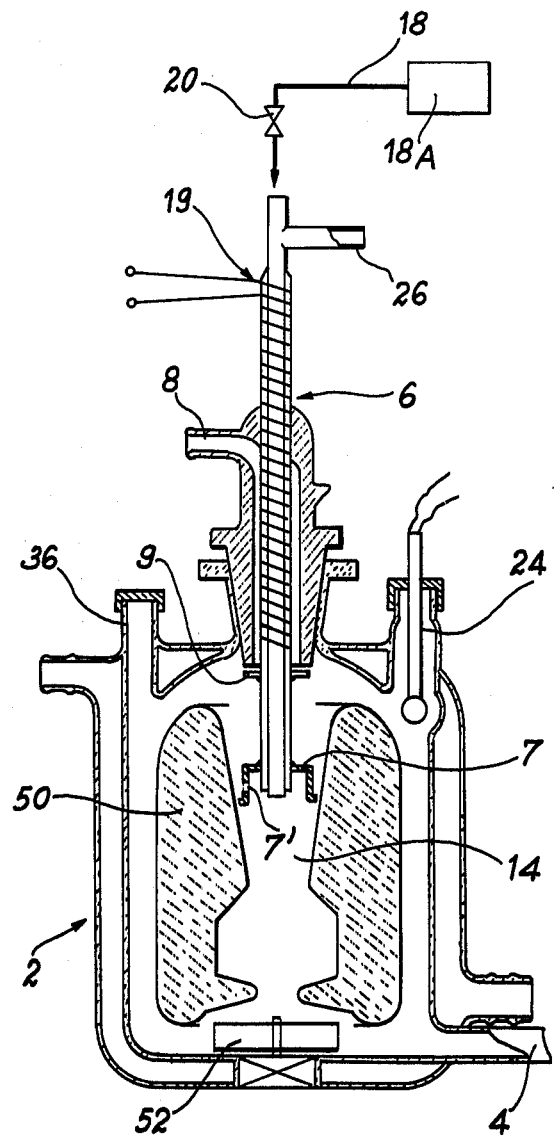
FIG. 2 is a vertical sectional view showing the cell of the device of FIG. 1, the cell being intended to contain a solution which is capable of dissolving the hydrochloric acid contained in said gases as these latter pass through said cell.

In FIG. 2, it is apparent that said cell 2 is provided internally with a toric body 50 of suitable shape and suitably arranged within said cell 2 in order to ensure good homogenization of said solution 14 with agitation at the time of passage of the gases by means of the magnetic bar 52.

By reason of the fact that the temperature of the incineration gases is in the vicinity of 150° C, the above-mentioned pipe 18 must accordingly be surrounded by a heating resistor (designated in FIG. 2 by the reference 19) in order to prevent any retention of hydrochloric acid by condensation of the gases against the walls of said pipe 18. It is also worthy of note that the lower end of said pipe 18 is adapted to carry a bell 7 pierced by orifices 7', said bell being intended to permit satisfactory contact between said solution 14 and the gases by formation of gas bubbles in said solution 14. A baffle 9 for preventing entrainment of solution with the gases is also fitted on said pipe 18 in the proximity of the gas outlet 8. It may also be noted that means (not shown) are provided for introducing said solution into said cell 2 at the inlet 4 at a temperature in the vicinity of 50° C.

Moreover, FIG. 1 shows that said valve 20 is connected by means of a threshold pH-meter 22 to an indicating electrode 24 associated with a reference electrode and immersed in the solution 14 of said cell 2 in order to control the admission of gases into said cell 2, taking into account the progressive variation in pH value of said solution as a result of dissolution of the hydrochloric acid.

The figure also shows that a communication can be established between the cell 2 and the surrounding atmosphere by means of the branch pipe 26 fitted with a valve 28 and that said cell can be drained-out by means of the pipe 30 fitted with a valve 32.

In FIG. 1, the references A and B designate circuits provided respectively for the circulation of the incineration gases which no longer contain hydrochloric acid and are drawn up by the vacuum pump 34 and for the circulation of the solution 14 which is withdrawn from said cell 2 at 36 by known means.

Said circuit A comprises successively:

a vessel 38 filled with an agent which is capable of retaining any traces of hydrochloric acid and chlorine in said gases as they pass from said cell 2, said agent being constituted for example by glass fibers impregnated with $Sr(OH)_2$ and copper chips;

a combustion chamber 40 in which the conditions of temperature (preferably of the order of 800° C) and of transfer of the gases are such that the organochlorine compounds contained in these gases are completely burnt;

a coulometric cell 42.

The circuit B comprises successively:

an assembly 44 of means of known type for withdrawing a given fraction of the solution 14 from said cell 2;

a coulometric cell 46 which is identical with the cell 42, said fraction of the solution 14 being added to the electrolytic solution of said cell 42.

It is recalled that a coulometric cell has two pairs of electrodes respectively for electrolysis and control of the potential of the solution and is fitted with means for measuring the quantity of electricity required for the electrolysis when the electrolyte solution contains a given type of ions such as chloride ions, for example, the quantity of which is to be determined. In the case of the coulometric cell of the device in accordance with the invention, the pair of electrodes for the control of potential comprises a reference electrode and a silver electrode and the pair of electrodes for the electrolysis comprises a silver anode and a platinum cathode whilst the electrolyte solution contains phosphoric acid and a small quantity of dibasic sodium phosphate and is maintained at a temperature in the vicinity of 20° C.

It can be noted that the function of the abovementioned electrolyte solution within the cell 42 is to dissolve the hydrochloric acid contained in the gases issuing from the chamber 40 as they pass through said cell 42.

Moreover, it is apparent from FIG. 1 that the aforesaid coulometric cells 42 and 46 are associated with a computer 48.

The principle of operation of the device shown diagrammatically in FIG. 1 for the analysis of a given fraction of a mixture of hydrochloric acid and organochlorine compounds contained in gases withdrawn in a suitable manner from an organochlorine compound incinerator is as follows:

after introduction of a given volume of the solution 14 into said cell 2, the valve 20 is opened and the vacuum pump 34 is started up, with the result that the gases withdrawn after incineration of organochlorine compounds are permitted to pass into said cell 2 through the solution 14, then into the combustion chamber 40 and finally into said coulometric cell 42;

closure of the valve 20 by means of the threshold pH-meter 22 connected to the electrode 24 makes it possible to pass into said cell 2 a predetermined fraction of said gases such that subsequent analytical determinations are possible with a sufficiently high degree of accuracy;

opening of the valve 28 after the valve 20 has been closed makes it possible to pass air into said cell 2 in order to entrain any organochlorine compounds which may have been solubilized within said cell.

The quantities $q$ and $Q$ can be determined by starting-up the units 42, 46 and 48.

The computer 48 is advantageously provided with a set of means which make it possible in conjunction with the equipment units of the device shown in FIG. 1 to initiate the analysis of a given fraction of said mixture in the manner indicated in the foregoing, to store the results of this analysis in memory and to initiate a further analysis. Thus, automatic sequential analysis of a mixture of hydrochloric acid and organochlorine compounds contained in gases can be carried out satisfactorily by means of the device shown in FIG. 1 and further provided with the set of means aforesaid. In consequence, the device is particularly suitable for carrying out automatic control of the destruction of organochlorine waste products as a result of incineration.

What we claim is:

1. A method for evaluating the extent of destruction by incineration of organochlorine compounds comprising the steps of:

passing gases derived from said incineration through a first alkaline solution which is capable of dissolving hydrochloric acid within said gases;

measuring the quantity of chloride ions, $Q$, contained in said first solution by coulometry to provide a value for the quantity of hydrochloric acid liberated at the time of said incineration;

absorbing the hydrochloric acid and the chlorine which are present in said incineration derived gases after they have passed through said first solution;

initiating combustion of the remaining gases subsequent to said absorption of the hydrochloric acid and the chlorine therefrom in order to burn the entire quantity of organochlorine compounds contained in said remaining gases;

passing the gases produced by combustion of the remaining gases through a second solution which is capable of dissolving the hydrochloric acid liberated by the organochlorine compounds at the time of said combustion of remaining gases;

measuring the quantity of chloride ions, $q$, contained in said second solution by coulometry;

calculating the ratio $q/Q$.

2. A method according to claim 1 including the step of passing a carrier gas through said first alkaline solution subsequent to said passage of incineration derived gases therethrough to entrain any organo-chlorine compounds retained therein.

3. A method according to claim 1 wherein the first solution is an alkaline solution of sodium bicarbonate and sodium sulphate.

4. A method according to claim 1 wherein said first solution is maintained at a temperature of the order of 50° C.

5. A method according to claim 1 wherein the quantity Q is measured in a given fraction of a given volume of said first solution.

6. A method according to claim 1 wherein said quantities $q$ and Q are measured at a temperature of about 20° C.

7. A method according to claim 1 wherein predetermined fractions of said gases corresponding to a given variation in the pH value of said first solution are analyzed successively by passing said fractions through said first solution.

8. A device for analyzing a mixture of hydrochloric acid and organochlorine compounds contained in gases, wherein said device comprises:

a cell for containing a first solution which is capable of dissolving said hydrochloric acid;

means for introducing said first solution into said cell;

means for passing said gases through said first solution;

a first coulometric cell for measuring the quantity of chloride ions Q contained in said first solution;

means for conveying said first solution from said cell into said first coulometric cell;

absorption means for absorbing the hydrochloric acid and the chlorine which are present in the remaining gases after they have passed through said first solution;

means for conveying said remaining gases from said cell to said absorption means;

a combustion chamber for carrying out the complete combustion of the remaining gases;

means for conveying said remaining gases from said absorption means to said combustion chamber;

means for retaining a second solution which is capable of dissolving the hydrochloric acid liberated by the organo-chlorine compounds at the time of said combustion of remaining gases;

means for passing the combustion gases produced by said remaining gases through said second solution;

means providing a second coulometric cell for measuring the quantity of chloride ions $q$ contained in said second solution, the solution of said second coulometric cell constituting said second solution;

thermostatically controlled means associated with said cell and with said means for measuring $q$ and Q;

means for calculating $q/Q$.

9. A device according to claim 8, wherein said device further comprises means for causing air to pass through the cell after the gases have been passed through said cell.

10. A device according to claim 8 wherein said cell comprises means defining a toric body having a central opening for receiving said passing gases; and an orifice containing a component positioned within said opening which permits formation of gas bubbles for effecting the contact of said first solution with said gases passing therethrough.

11. An analytical device according to claim 8 wherein said device further comprises means for introducing a given volume of said first solution into said cell and means for withdrawing a given fraction of said first solution after passage of said gases.

12. A device according to claim 8 for sequential analysis of a mixture of hydrochloric acid and organochlorine compounds contained in gases, wherein said device further comprises means for passing through said first solution a predetermined fraction of said gases corresponding to a given variation in the pH value of said first solution by passing said fraction through said first solution.

13. An automatic device according to claim 8 for sequential analysis of a mixture of hydrochloric acid and organochlorine compounds contained in gases, wherein said device further comprises:
means for initiating the analysis of a given fraction of said gases;
means for storing the results of said analysis in memory;
means for initiating a further analysis.

14. The method according to claim 3 wherein said first solution is maintained at a temperature of the order of 50° C.

15. A method according to claim 3 wherein the quantity, Q, is measured in a given fraction of a given volume of said first solution.

16. A method according to claim 4 wherein the quantity, Q, is measured in a given fraction of a given volume of said first solution.

17. A method according to claim 3 wherein said quantities $q$ and Q are measured at a temperature of about 20° C.

18. A method according to claim 4 wherein said quantities $q$ and Q are measured at at temperature of about 20° C.

19. A method according to claim 5 wherein said quantities $q$ and Q are measured at a temperature of about 20° C.

20. A method according to claim 3 wherein predetermined fractions of said gases corresponding to a given variation in the pH value of said first solution are analyzed successively by passing said fractions through said first solution.

21. A method according to claim 4 wherein predetermined fractions of said gases corresponding to a given variation in the pH value of said first solution are anaylzed successively by passing said fractions through said first solution.

22. A method according to claim 5 wherein predetermined fractions of said gases corresponding to a given variation in the pH value of said first solution are analyzed successively by passing said fractions through said first solution.

23. A method according to claim 6 wherein predetermined fractions of said gases corresponding to a given variation in the pH value of said first solution are analyzed successively by passing said fractions through said first solution.

24. A device according to claim 9 wherein said cell comprises means defining a toric body having a central opening for receiving said passing gases; and an orifice containing a component positioned within said opening which permits formation of gas bubbles for effecting the contact of said first solution with said gases passing therethrough.

25. An analytical device according to claim 9 wherein said device further comprises means for introducing a given volume of said first solution into said cell and means for withdrawing a given fraction of said first solution after passage of said gases.

26. An analytical device according to claim 10 wherein said device further comprises means for introducing a given volume of said first solution into said cell and means for withdrawing a given fraction of said first solution after passage of said gases.

27. A device according to claim 9 for sequential analysis of a mixture of hydrochloric acid and organochlorine compounds contained in gases, wherein said device further comprises means for passing through said first solution a predetermined fraction of said gases corresponding to a given variation in the pH value of said first solution by passing said fraction through said first solution.

28. A device according to claim 10 for sequential analysis of a mixture of hydrochloric acid and organochlorine compounds contained in gases, wherein said device further comprises means for passing through said first solution a predetermined fraction of said gases corresponding to a given variation in the pH value of said first solution by passing said fraction through said first solution.

29. A device according to claim 11 for sequential analysis of a mixture of hydrochloric acid and organochlorine compounds contained in gases, wherein said device further comprises means for passing through said first solution a predetermined fraction of said gases corresponding to a given variation in the pH value of said first solution by passing said fraction through said first solution.

30. An automatic device according to claim 9 for sequential analysis of a mixture of hydrochloric acid and organochlorine compounds contained in gases, wherein said device further comprises:
means for initiating the analysis of a given fraction of said gases;
means for storing the results of said analysis in memory;
means for initiating a further analysis.

31. An automatic device according to claim 10 for sequential analysis of a mixture of hydrochloric acid and organochlorine compounds contained in gases, wherein said device further comprises:
means for initiating the analysis of a given fraction of said gases;
means for storing the results of said analysis in memory;
means for initiating a further analysis.

32. An automatic device according to claim 11 for sequential analysis of a mixture of hydrochloric acid and organochlorine compounds contained in gases, wherein said device further comprises:
means for initiating the analysis of a given fraction of said gases;

means for storing the results of said analysis in memory;

means for initiating a further analysis.

33. An automatic device according to claim 12 for sequential analysis of a mixture of hydrochloric acid and organochlorine compounds contained in gases, wherein said device further comprises;

means for initiating the analysis of a given fraction of said gases;

means for storing the results of said analysis in memory;

means for initiating a further analysis.

* * * * *